United States Patent [19]
Koizumi et al.

[11] Patent Number: 5,366,858
[45] Date of Patent: Nov. 22, 1994

[54] METHOD OF AND APPARATUS FOR DETECTING MICROORGANISMS

[75] Inventors: Naohisa Koizumi, Kawasaki; Shokichi Nakajima, Machida; Naoki Yuguchi; Kazumi Tanaka, both of Yokohama, all of Japan

[73] Assignees: Canon Kabushiki Kaisha; Meiji Seika Kaisha, both of Tokyo, Japan

[21] Appl. No.: 946,775

[22] Filed: Sep. 18, 1992

Related U.S. Application Data

[63] Continuation of Ser. No. 454,648, Dec. 21, 1989.

[30] Foreign Application Priority Data

Dec. 23, 1988 [JP] Japan .................. 63-324987

[51] Int. Cl.$^5$ .................................... G01N 33/53
[52] U.S. Cl. ........................ 435/5; 435/7.1; 435/7.21; 435/7.32; 436/517
[58] Field of Search .............. 435/5, 7.21, 960, 967, 435/7.1, 7.32; 436/517; 424/3, 7.1

[56] References Cited

U.S. PATENT DOCUMENTS

| | | | |
|---|---|---|---|
| 2,656,508 | 10/1953 | Coulter | 324/71 |
| 4,246,343 | 1/1981 | Wilkins et al. | 435/32 |
| 4,618,576 | 10/1986 | Rosenstein et al. | 435/7 |
| 4,622,298 | 11/1986 | Mansour et al. | 435/34 |
| 4,661,913 | 4/1987 | Wu et al. | 364/500 |
| 4,683,212 | 7/1987 | Uffenheimer | 436/52 |
| 4,732,479 | 3/1988 | Tanaka et al. | 356/336 |

FOREIGN PATENT DOCUMENTS 29622 2/1984 Japan .

OTHER PUBLICATIONS

Antibody as a Tool Edited by Marchalonis & Warr Published by Wiley & Sons 1982 pp. 112, 113, 158–161.
Schleif, Robert F., "Genetics and Molecular Biology", pp. 290–293, published by Addison-Wesley Publishing Co., 1986.
Sambrook, et al., "Molecular Cloning", A Laboratory Manual, 2nd Ed., pp. 18.60–18.75, Cold Spring Harbor Laboratory Press, 1989.
Infecton and Immunity, vol. 54, (Oct. 1986), pp. 222–227, V. Hopwood, et al., "A Monoclonal Antibody to a Cell Wall Component of *Candida albicans*".
Melamed et al., Flow Cytometry and Sorting, pp. 61–63 (1979).
Van Dilla et al., Flow Cytometry: Instrumentation and Data Analysis, pp. 117–118 (1985).

*Primary Examiner*—Christine M. Nucker
*Assistant Examiner*—Jeffrey Stucker
*Attorney, Agent, or Firm*—Fitzpatrick, Cella, Harper & Scinto

[57] ABSTRACT

The present invention provides a method of detecting microorganisms, comprising the step of converting physical forms of microorganisms by antigen-antibody reaction and successively measuring the information that shows the physical forms of the converted data, and the step of comparing a statistical pattern of the values thus measured and a reference statistical pattern of a control subjected to no antigen-antibody reaction, thus detecting the microorganisms of interest. A change in both patterns, i.e., no correspondence thereof, enables recognition of the presence of the microorganisms of interest.

7 Claims, 6 Drawing Sheets

METHOD OF AND APPARATUS FOR DETECTING MICROORGANISMS

This application is a continuation of application Ser. No. 07/454,648 filed Dec. 21, 1989, now abandoned.

BACKGROUND OF THE INVENTION

1. Field of the invention

The present invention relates to a method of, and an apparatus for, detecting or identifying microorganisms of interest contained in a specimen.

2. Related Background Art

Detection and identification of microorganisms have been hitherto made by culture examination. This is a method in which a plurality of culture mediums suited to the multiplication of microorganisms are prepared, samples are inoculated to the mediums so that the microorganisms are cultured, and the properties of the microorganisms thus grown are examined by various test methods such as morphological examination and biochemical examination.

In recent years, the agglutination method has also been developed, in which the agglutination of microorganisms, caused by antigen-antibody reaction using antibodies specific to various microorganisms, is recognized with the naked eye.

The culture method, however, takes a long time for the culture and also requires examinations on many items. In usual instances, it takes two or three days at minimum until the examinations are completed, so that, in some cases, patients have deceased before something has come out of the examination, as in diagnosis of infectious diseases. Some kinds of microorganisms also have the problems such that in some instances they are susceptible to death, can be cultured with difficulty, and thus can not be detected.

The agglutination method is a method that enables detection of even dead microorganisms, can be operated with relative simplicity, and can achieve a rapid examination. This, however, is a method in which the agglutination of microorganisms, caused by antigen-antibody reaction, is observed with the naked eye, so that microorganisms present in a small quantity can not be detected. The subjective views of the observer also tend to enter into his or her judgement, so that it may sometimes even occur that the results of examination are different when observed by different persons. Moreover, this method has the problems that the results of examination can not be objectively represented in numerical values or graphs and also the data obtained can not be stored.

On the other hand, beside these methods, a method is known in which individual fine particles in a specimen are optically measured using so-called flow cytometry techniques and the types of microorganisms are detected and classified based on its statistical tendency. Details thereof are disclosed in U.S. Pat. No. 4,661,913. The detection and classification method can be outlined as follows: Any correspondence of a statistical pattern of optical response, obtained by measurement, to a statistical pattern of known microorganisms, previously given, is sought after. When pattern forms are identical, the presence of a microorganism corresponding to the pattern is recognized.

In general, however, many kinds of fine particles other than the microorganisms of interest are present in the specimen unless purification is carried out. Hence, if other microorganisms or noise components that are similar to the microorganisms of interest in the measured values from the optical response are contained in the specimen, the noise components can not be distinguished from the microorganisms of interest. That is to say, it is difficult to form specifically only the microorganisms of interest into a pattern among many noise components. Even when the patterns are identical, it is impossible to confirm whether the pattern can really correspond to the microorganisms of interest whether it corresponds to the noise components. Thus, the method disclosed in U.S. Pat. No. 4,661,913 has the problems of low detection accuracy and poor reliability.

SUMMARY OF THE INVENTION

An object of the present invention is to provide a method of, and an apparatus for, detecting the microorganisms of interest contained in a specimen, with a good accuracy and in a short time.

Another object of the present invention is to provide an apparatus that has automated the detection of the microorganisms of interest contained in a specimen to enable detection in an objective manner.

Still another object of the present invention is to enable specific detection of only the microorganisms of interest with a good accuracy, even when other microorganisms or noise components are present in a specimen in addition to the microorganisms of interest.

The present invention provides a method of detecting microorganisms, comprising the steps of;
  reacting an antibody capable of binding specifically to a microorganism of interest, with a specimen to give a reacted sample;
  successively measuring optical response of the fine particles contained in said reacted sample;
  comparing a statistic of measured values obtained by said measurement and a statistic of the optical response of the fine particles contained in a control sample not reacted with said antibody; and
  detecting the microorganism of interest contained in the specimen as a result of said comparison.

The present invention also provides an apparatus for detecting microorganisms, comprising the means for;
  successively causing fine particles in a reacted sample obtained by reacting with a specimen an antibody capable of binding specifically to a microorganism of interest, to pass through a detecting section;
  irradiating said detecting section with light;
  measuring optical response of the fine particles subjected to said irradiation with light;
  comparing a statistic of measured values obtained by said measurement and a statistic of measured values of the optical response of a control sample not reacted with said antibody; and
  detecting the microorganism of interest contained in the specimen as a result of said comparison.

Other additional and preferred embodiments of the above method and apparatus will become apparent from the following descriptions.

DESCRIPTION OF THE PREFERRED EMBODIMENTS

[Detection method]

Stated summarily, the method of detecting microorganisms according to the present invention comprises the step of converting physical forms of microorganisms by antigen-antibody reaction and successively measuring the information that shows the physical forms of the converted data, and the step of comparing a statistical pattern of the values thus measured and a reference statistical pattern of a control subjected to no antigen-antibody reaction, thus detecting the microorganisms of interest.

When, for example, an optically measured value is used, the microorganisms of interest and an antibody reacting specifically to said microorganisms are added in a specimen in the former step to cause them to react, and converted into a state where optical response or changes in optical response of the microorganisms may be caused. Then, the resulting reacted samples is subjected to successive measurement of the optical response of the reaction product formed between the microorganism and antigen. In the latter step, a statistical pattern resulting from a statistical process of the measured values obtained by the measurement and a statistical pattern of the measured values of a control sample not reacted with the above antibody are compared to catch the changes of patterns, and thus the presence of the microorganisms of interest contained in the specimen can be detected.

Thus, it follows that, when the statistical patterns of the measured values in the above reacted sample and control sample are compared, both statistical patterns are different from each other in a sample in which the microorganisms of interest are present, and both statistical patterns show no difference in a sample in which the microorganisms of interest are not present.

According to the present invention, the results of examination can be objectively obtained, and also only the microorganisms of interest can be detected specifically even when fine particles other than the microorganisms of interest, as exemplified by microorganisms of different kinds and noise components such as cells, dust and fluorescent substances are present together in the specimen.

An example of methods preferable for the above successive measurement include a flow cytometry. The flow cytometry is a method in which particles, i.e., in the present invention the fine particles in the specimen containing the antigen-antibody reaction product between the microorganisms of interest and the antibody, are individually separated using the sheath-flow system and flowed to a detecting section to which an energy used for measurement is applied, where the information relating to the volume or properties of a fine particle is measured. As methods of obtaining the information of the particle, an optical measuring method or electrical measuring method is commonly used. The optical measuring method refers to a method in which the detecting section is irradiated with light such as a laser beam or ultraviolet light so that an optical response as exemplified by the emission of scattered light or transmitted light or the fluorescence, resulting from the irradiation with light on the particle in the detecting section, is measured, where the size, form or properties of the particle is examined. The electrical measuring method refers to a method in which a high-frequency electric current is flowed through a liquid in a detecting section, and changes in electrical impedance, caused by the particle passing through the detecting section, are caught so that the volume of the particle is measured.

In the present invention, when the optical measuring method is employed, it is also possible to use a method in which the scattered light from or transmitted light through the particle is measured, a method in which the scattered light and fluorescence are simultaneously measured. In the present invention, when the microorganisms are detected and identified by measuring the intensity of fluorescence, it is also possible to use a method in which the antibody reacting with the microorganisms of interest is previously labelled using a fluorescent substance, or a method in which a microorganism and an antibody are bound and a fluorescent substance capable of binding to said antibody is bound. Of course, both methods may also be used together.

The antibody specific to the microorganisms of interest includes any of a polyclonal antibody and a monoclonal antibody. Such antibodies can be obtained by any methods, e.g., animal immunization using a microbial antigen, cell fusion of antibody-producing cells of the required antibody, and genetic engineering using a gene that codes for the required antibody.

Known substances can be used as the fluorescent substance which is bound to the antibody, including, for example, fluorescein isothiocyanate (FITC), rhodamin X isothiocyanate (XRITC), tetramethyl rhodamin isothiocyanate (TRITC), and phycoerythrin (PE). The labelling of all the above antibodies by these fluorescent substances can be carried out by known means. For example, an antibody solution (a phosphate buffer solution) adjusted to a suitable concentration is adjusted to pH 9.1 to 9.5 using a sodium carbonate buffer solution, to which a necessary amount of FITC powder is added, and the mixture is reacted at a low temperature for about 6 hours with stirring, followed by removal of unreacted fluorescent coloring matters by gel filtration or the like and also purification by column chromatography using DEAE-cellulose or the like. A labelled antibody can be thus obtained.

It is also possible to subject an antibody reacting to the above specific antibodies to fluorescent labelling, and bind the resulting antibody to the above particular antibody, thus indirectly labelling the specific antibodies.

The specimen from which microorganisms can be detected and identified includes body fluids such as blood, urine and saliva, biocomponents such as tissues, food, water of rivers, culture solutions of microorganisms, and suspensions of microorganisms.

The microorganism capable of being detected are microorganisms that may exhibit an antigen-antibody reaction, i.e., agglutination reaction, such that the statistical pattern of measured values in the above reacted sample is different from the statistical pattern of measured values in the control sample. Such microorganisms include various ones such as bacteria, yeast, Eymycetes, and rickettsia. Examples of such microorganisms include *Pseudomonas aeruginosa, Staphylococcus aureus, Escherichia coli, Entterobacter chloacae, Citrobacter freundii, Candida albicans, Klebsiella pneumoiae, Serfaria marcescens, Proteus mirabills, Streptococcus faecalis,* and *Lactobacillus casei.*

In the present invention, the measured values obtained are statistically processed and formed into a pattern. As methods of expressing what has been formed into a pattern by statistical processing, a histogram or a cytogram as used in Examples described below is suited as an example.

[Detecting apparatus]

The apparatus for detecting microorganisms according to the present invention applies the above detecting method as a fundamental principle. An embodiment in which the optical measuring method is employed will be described below.

Figure 1:
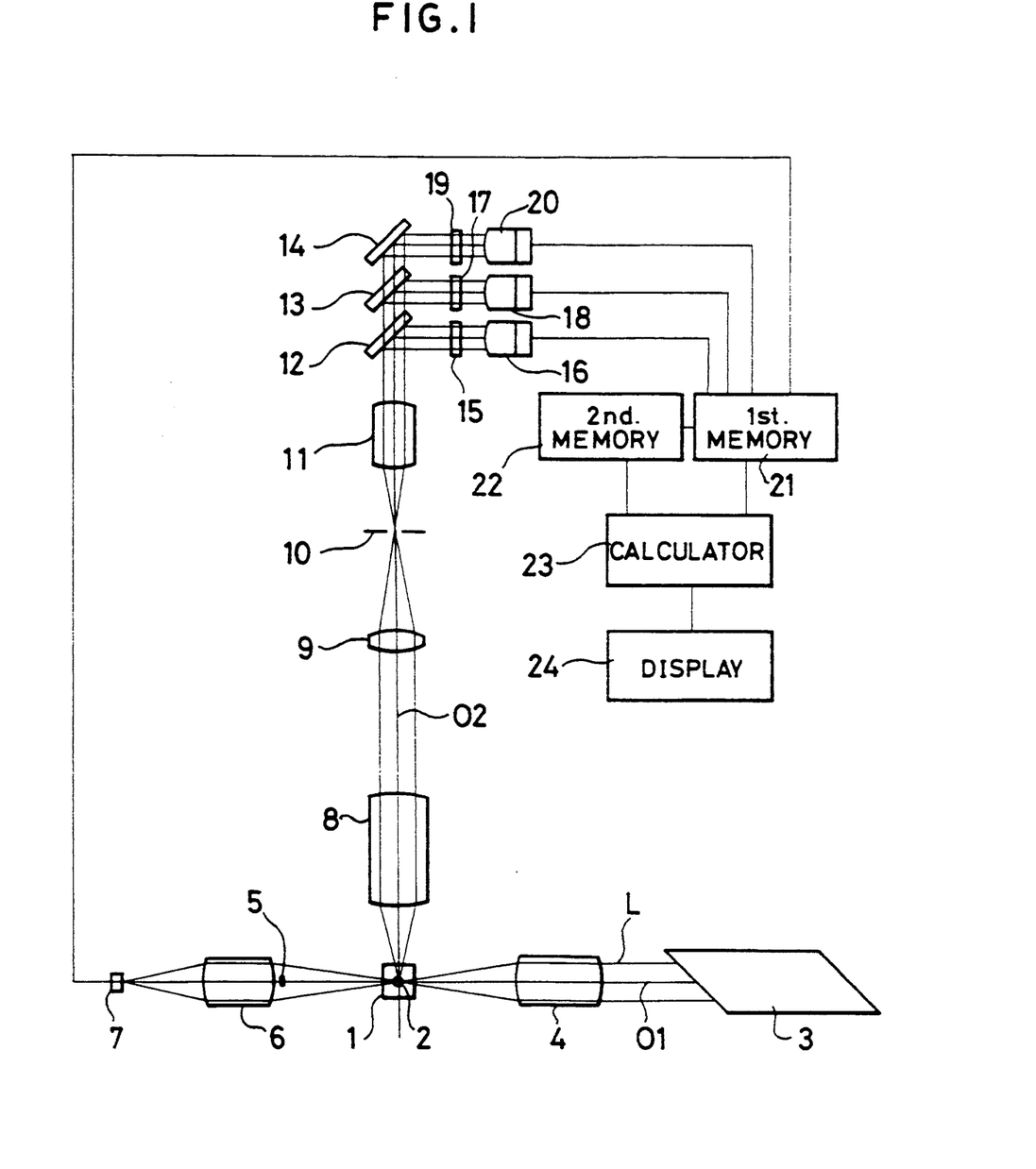
FIG. 1 illustrates the constitution of an apparatus for detecting microorganisms according to the present invention.

FIG. 1 illustrates the constitution of an example of an apparatus for detecting microorganisms according to the present invention. At the center of a flow cell 1, a flow passage 2 is provided, through which a specimen containing the microorganisms of interest such as bacteria in a floating state passes in the vertical direction viewed in the drawing. This flow passage is so designed that the individual fine particles in the specimen may be separated one by one and successively flow in a single line by the known sheath-flow system. A laser-beam light source 3 is provided in the direction falling at right angles with the direction of the flow at this flow passage 2. On the axis of light beam 01, an image formation lens 4 that adjusts a laser beam L to a elliptical spot comprising any desired major axis and minor axis is provided so that the light irradiated from the laser-beam light source 3 can be shed on the flow passage 2. As an example of the image formation lens 4, a combination of cylindrical lenses, etc. are used. As a result of the passing of a matter to be detected such as bacterium, through the detecting section irradiated with the laser beam, scattered light is emitted from the matter to be detected. Fluorescence is also produced if the matter to be detected has been subjected to fluorescent labelling. Among the scattered light rays, the forward scattered light with a given angle component, emitted in the forward direction of the axis of the irradiated laser light beam, is condensed with an objective lens 6, and its intensity is detected with a photoelectric detector 7. In general, the information concerning the size of the matter to be detected is obtained from the forward scattered light. A stopper 5 plays a role of preventing strong direct light or transmitted light: of the laser beam from entering into the photoelectric detector 7, so that only the scattered light is detected by the photoelectric detector 7. The present embodiment takes the form in which transmitted light is not detected. The transmitted light, however, may also be detected to serve as a measurement parameter.

In order to detect sideward scattered light and fluorescence, an objective lens 8, a condenser lens 9, a diaphragm 10, a condenser lens 11, dichroic mirrors 12 and 13, a mirror 14 are sequentially provided on the axis of light beam 02 forwarding in the direction falling at right angles with the axis of the irradiated laser light beam 01. In the reflection direction of the dichroic mirror 12, a barrier filter 15 and a photoelectric detector 16 for detecting sideward scattered light are provided. In the reflection direction of the dichroic mirror 13, a barrier filter 17 and photoelectric detector 18 for detecting red fluorescence are provided, and also in the reflection direction of the mirror 14, a barrier, filter 19 and a photoelectric detector 20 for detecting green fluorescence are provided. Photomultipliers that multiply the intensity of weak light to a detectable level are used in these photoelectric detectors 16, 18 and 20.

Electric signals detected by the photoelectric detectors 7, 16, 18 and 20 are inputted in a first memory 21 and stored there. In a second memory 22, the data of the first memory 21 are previously forwarded and stored. The contents of the data of the first memory 21 and second memory 22 are compared in a comparison calculator 23, and thus whether or not the statistical patterns of the data are identical to each other is detected using a pattern recognition processing technique. Histograms or cytograms are used in the statistical processing of the data. The results of the statistical processing, expressed by the histograms or cytograms, and the results of comparison and calculation are displayed on a display unit 24.

A method of detecting and identifying the microorganisms in a specimen by the use of the above apparatus will be described below.

Figure 6:
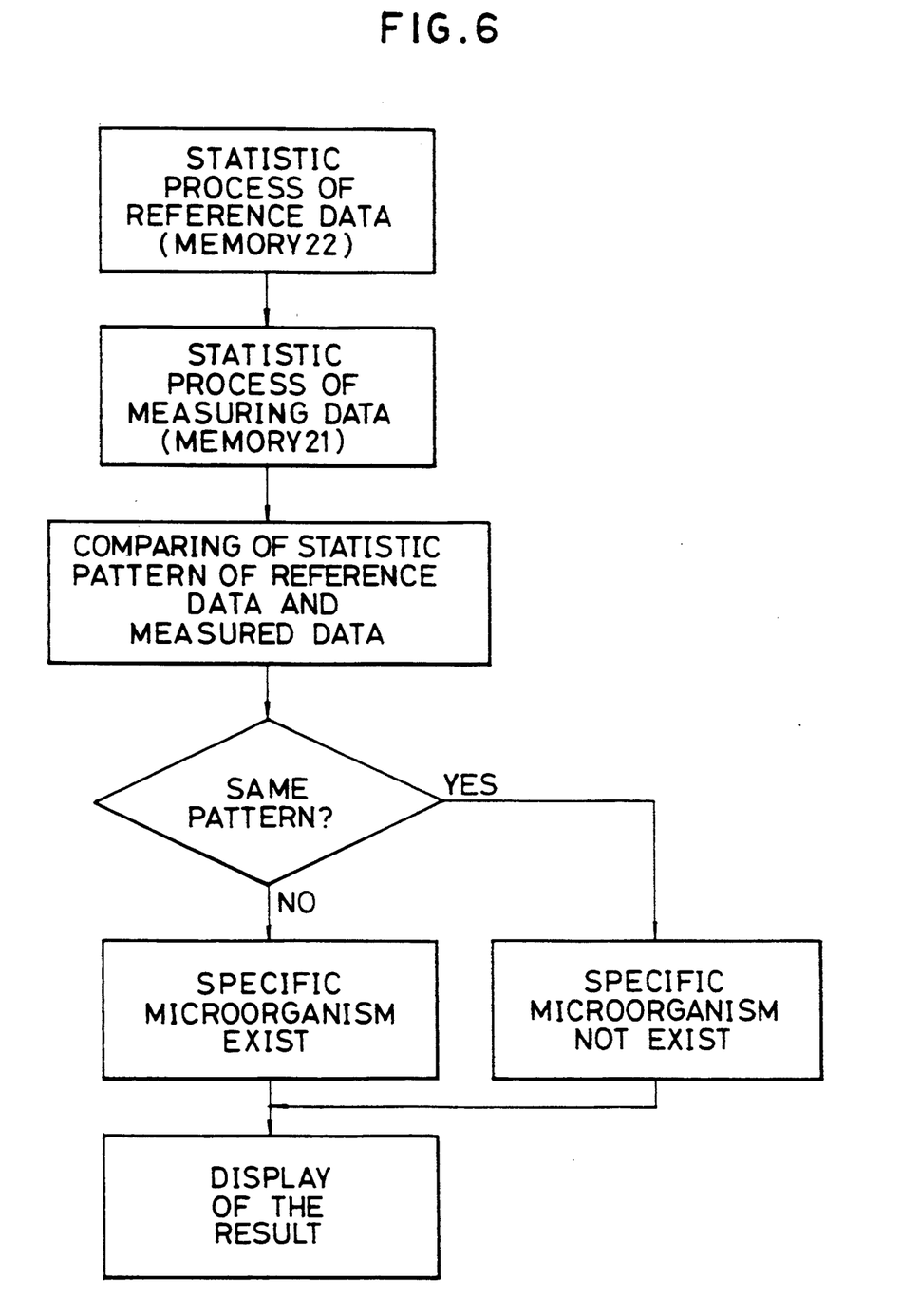
FIG. 6 is a flow chart showing an operational procedure in an arithmetic logic unit.

First, a sample (control sample) obtained by adding no antibody to a specimen containing microorganisms is measured using the above apparatus. The data obtained by the measurement and stored in the first memory 21 are forwarded to the second memory 22, where the data are stored as reference data. Next, a sample (reacted sample) obtained by reacting with the above specimen a monoclonal antibody reacting specifically with particular microorganisms is measured using the above apparatus. The data obtained by this measurement are stored in the first memory 21 The adding of the monoclonal antibody in the specimen causes antigen-antibody reaction when the microorganisms of interest are present, and microorganisms agglutinate each other to form clumps of microorganisms. This results in an increase in the apparent size of microorganisms, which appears as a change in the intensity of scattered light or the intensity of transmitted light. When the antibody is labelled, an increase in size of microorganisms results in an increase in the amount of fluorescence used for the labelling and also an increase in the intensity of fluorescence to be measured. In the calculator 23, the contents in the second memory 22 in which the reference data are stored and in the first memory in which the measuring data are stored are compared and whether or not the statistical patterns of the data expressed by histograms or cytograms are identical is detected. When the antigen-antibody reaction has taken place, the measuring light pattern changes with respect to the reference pattern, so that the presence of the microorganisms of interest can be recognized. When the microorganisms of interest are not present, no antigen-antibody reaction takes place, and therefore no changes of pattern may occur. FIG. 6 shows a flow chart of the procedure of these processes carried out in the calculator 23.

It is also possible not only to detect whether or not the microorganisms are present, but also to quantitatively measure the microorganism by comparing a calibration curve previously prepared and the measuring data.

The foregoing describes an embodiment of an apparatus in which an energy for optical measurement is exerted on the fine particles from the laser beam light source, and the physical form of the fine particles are measured by optical means. As another method, however, a high-frequency current may be previously flown to the liquid present at the small hole at the detecting section by providing an energy for electrical measurement, i.e., an electrode, and then the changes of electrical impedance, caused by the pass of fine particles, may be calculated to measure the volume information of fine particles. The microorganisms can be thus also detected similarly.

EXPERIMENT 1

An example of detecting and identifying the microorganisms in a specimen by the use of the apparatus described above will be described below.

A colony obtained by culturing blood collected from a patient was scraped out and suspended in a phosphate buffer physiological saline solution (PBS) in which 1% of bovine serum albumin (BSA) was added. The resulting suspension was allowed to stand at room temperature for 1 hour to give control sample 1. In a test tube, 0.5 ml of specimen 1 was taken, and 0.5 ml of a solution of an anti-*Pseudomonas aeruginosa* monoclonal antibody (0.1 mg/ml) prepared according to the method as disclosed in Japanese Unexamined Patent Publication No. 29622/1984 was added therein and blended. The reaction was carried out at room temperature for 1 hour. The reaction mixture was then centrifugally separated at 3,500 r.p.m. for 10 minutes, the supernatant was removed, and the precipitate was suspended in 2 ml of PBS in which 0.1% of BSA was added. Reacted sample 1 was thus obtained. These control sample 1 and reacted sample 1 were subjected to measurement of scattered light and analysis, using the apparatus described above. As a result, *Pseudomonas aeruginosa* was detected.

Figure 2A:
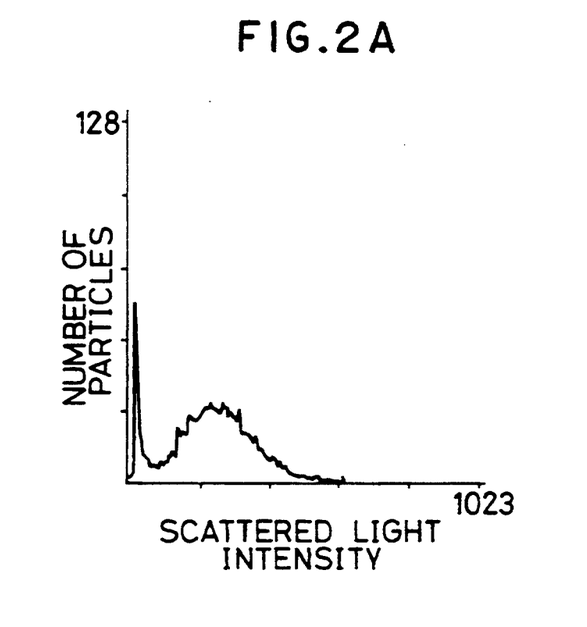
FIGS. 2A and 2B are explanatory views of an example in which Pseudomonas aeruginosa is detected using scattered light.
Figure 2B:
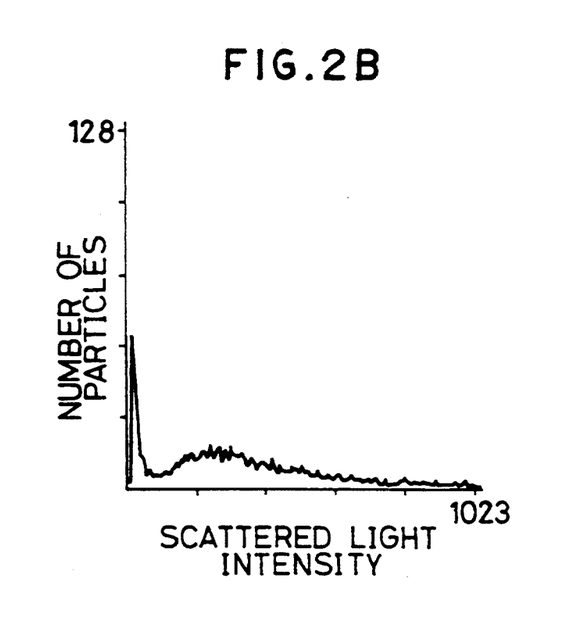

FIGS. 2A and 2B are plotted with scattered light intensity as the abscissa and number of particles as the ordinate, respectively. FIG. 2A shows the results of measurement of the control sample 1, and FIG. 2B, the results of measurement of reacted sample 1. Compared with FIG. 2A, the histogram in FIG. 2B shifted to the right direction, and thus there is seen an increase in the particles having a strong scattered light intensity. This is because the mixing of *Pseudomonas aeruginosa* with anti-*Pseudomonas aeruginosa* monoclonal antibody resulted in the agglutination of *Pseudomonas aeruginosa* to increase the apparent size of *Pseudomonas aeruginosa*, bringing about the emission of stronger scattered light. An additional biological property test also confirmed that the microorganism was *Pseudomonas aeruginosa*

Experiment 2

In a test tube, 0.5 ml of the control sample 1 obtained in Experiment 1 was taken, and 0.5 ml of a solution of an anti-*Pseudomonas aeruginosa* monoclonal antibody was added therein and mixed. The reaction was carried out at room temperature for 1 hour. The reaction mixture was then centrifugally separated at 3,500 r.p.m. for 10 minutes, and the supernatant was removed (cleaning operation). This cleaning operation was repeated three times, and the precipitate was suspended in a solution of FITC-labelled anti-mouse immunoglobulin antibody, followed by reaction at room temperature for 1 hour. Next, after further cleaning operation, the precipitate was suspended in 2 ml of PBS in which 0.1% of BSA was added. Reacted sample 2 was thus obtained. These control sample 1 and reacted sample 2 were subjected to measurement of fluorescence and analysis, using the apparatus described above. As a result, *Pseudomonas aeruginosa* was detected.

Figure 3A:
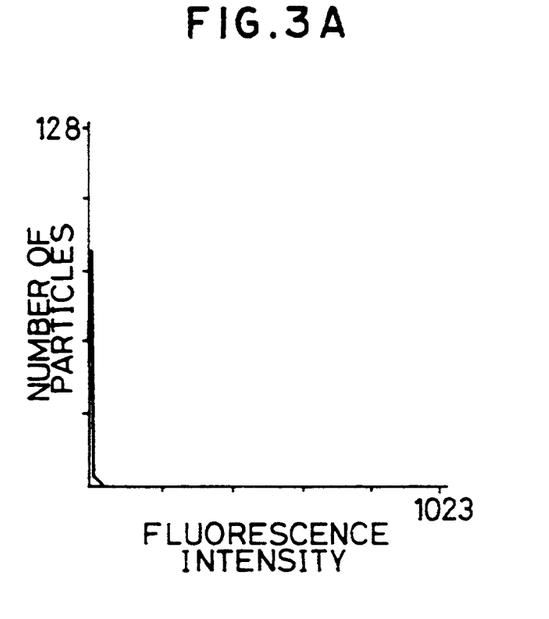
FIGS. 3A and 3B are explanatory views of an example in which *Pseudomonas aeruginosa* is detected using fluorescence.
Figure 3B:
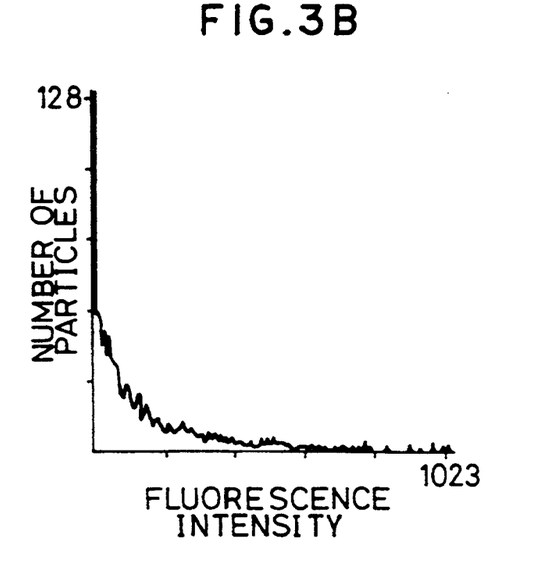

FIGS. 3A shows the results of measurement of the control sample 1, and FIG. 3B, the results of measurement of reacted sample 2. As FIGS. 3A and 3B show, particles showing fluorescence are little present in the control sample 1, but on the other hand an increase in particles showing strong fluorescence was seen in the reacted sample 2. This is because the mixing of the *Pseudomonas aeruginosa* and anti-*Pseudomonas aeruginosa* monoclonal antibody formed a bound product, to which the FITC-labelled anti-mouse immunoglobulin antibody binding to the anti-*Pseudomonas aeruginosa* monoclonal antibody was further bound, and this bound product generated fluorescence because of FITC. An additional biological property test also confirmed that the microorganism was *Pseudomonas aeruginosa*.

Experiment 3

A colony obtained by culturing blood of a patient was scraped out and suspended in PBS in which 1% BSA was added. The resulting suspension was allowed to stand at room temperature for 1 hour to give control sample 2. In a test tube, 0.5 ml of specimen 2 was taken, and 0.5 ml of a solution of an anti-*Candida albicans* monoclonal antibody (0.1 mg/ml) prepared according to the method as disclosed in Infect. Immun., 54, No. 1, pp.222-227, 1986, was added. The reaction was carried out at room temperature for 1 hour. Next, the cleaning operation was repeated three times, and the precipitate was suspended in a solution of FITC-labelled anti-mouse immunoglobulin antibody, followed by reaction at room temperature for 1 hour. Next, after further cleaning operation, the precipitate was suspended in 2 ml of PBS in which 0.1% of BSA was added. Reacted sample 3 was thus obtained. These control sample 2 and reacted sample 3 were subjected to measurement of fluorescence and analysis, using the apparatus described above. As a result, *Candida albicans* was detected.

Figure 4A:
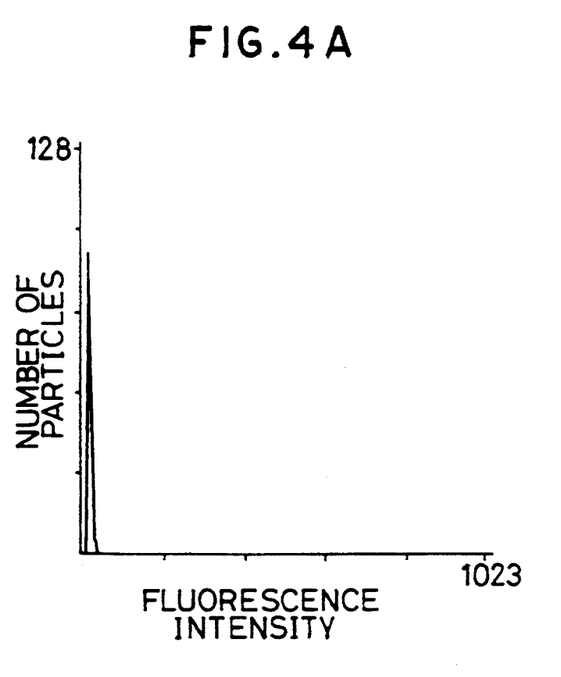
FIGS. 4A and 4B are explanatory views of an example in which *Candida albicans* is detected using fluorescence.
Figure 4B:
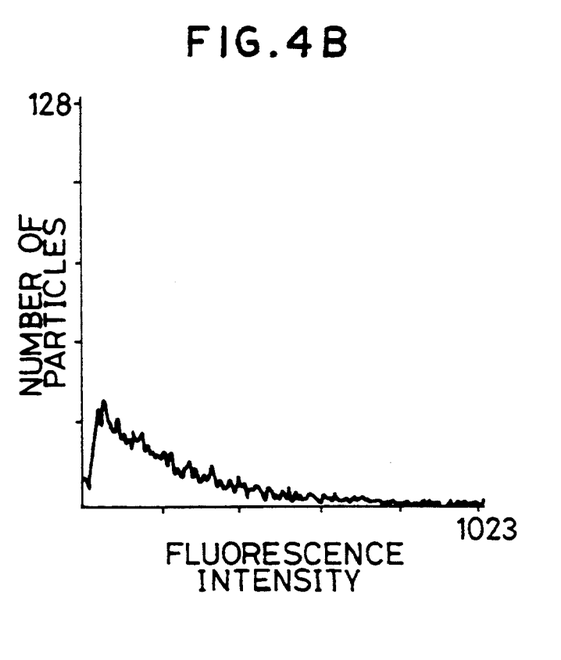

FIGS. 4A shows the results of measurement of the control sample 2, and FIG. 4B, the results of measurement of reacted sample 3. As FIGS. 3A and 3B show, comparison of the control sample 2 and reacted sample 3 showed an increase in particles showing strong fluorescence was seen in the reacted sample 3. This is because to a bound product of the *Candida albicans* and anti-*Candida albicans* antibody, the FITC-labelled anti-mouse immunoglobulin antibody binding to the anti-*Candida albicans* monoclonal antibody was further bound, and this bound product generated fluorescence because of FITC. An additional biological property test also confirmed that the microorganism was *Candida albicans*.

EXPERIMENT 4

The control sample 1 and reacted sample 2 in Experiment 2 previously described were subjected to measurement of scattered light and fluorescence, using the apparatus described above. As a result, *Pseudomonas aeruginosa* was detected.

Figure 5A:
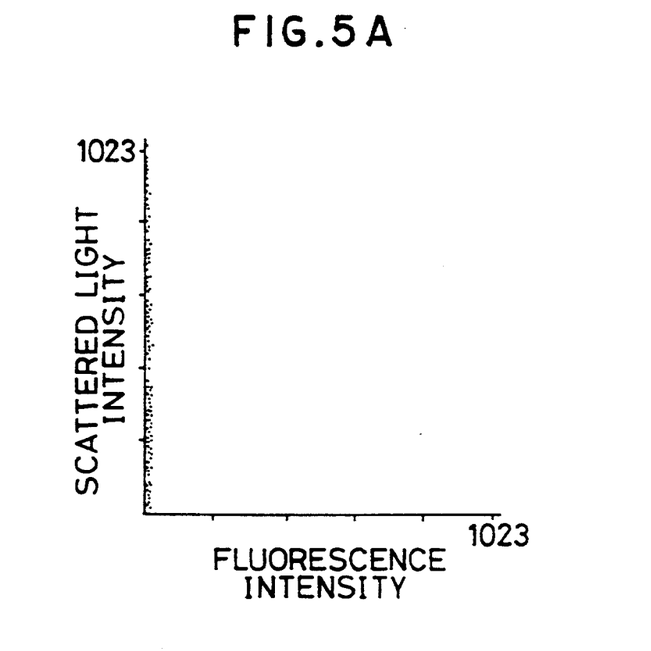
FIGS. 5A and 5B are explanatory views of an example in which *Pseudomonas aeruginosa* is detected using scattered light and fluorescence.
Figure 5B:
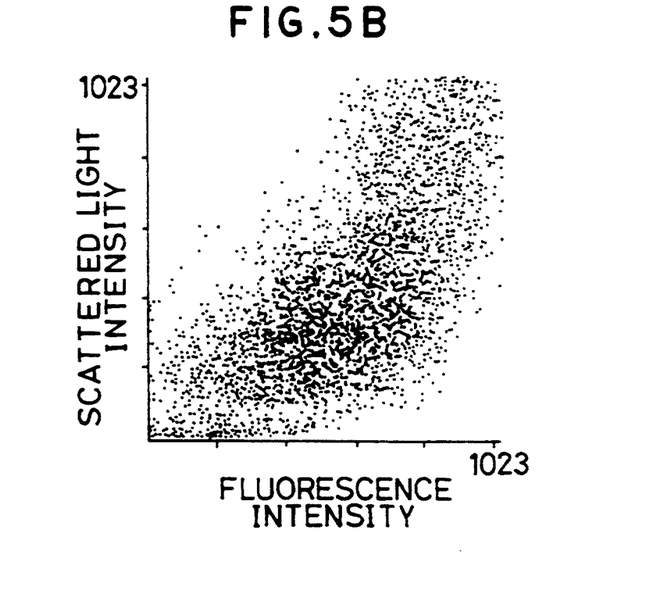

FIGS. 5A and 5B are plotted with fluorescence intensity as the abscissa and scattered light intensity as the ordinate, respectively. FIG. 5A shows the results of measurement of the control sample 1, and FIG. 5B, the results of measurement of reacted sample 1.

We claim:

1. A method of detecting the presence or absence of a microorganism of interest in a sample comprising the steps of:

provmding a reacted sample which is reacted with an antibody capable of binding specifically to said microorganism of interest, wherein a plurality of said microorganisms of interest agglutinate each other to form clumps of said microorganisms of interest by antigen-antibody reaction;

providing a non-reacted sample which is not reacted with said antibody;

measuring optical response of suspended substances in said non-reacted sample;

measuring optical response of suspended substances including said clumps in said reacted sample;

comparing statistics of measured values obtained by said measurements of said non-reacted sample and said reacted sample; and determining the presence or absence of said microorganism of interest in said sample as a result of said comparison, wherein said microorganism of interest is determined to be absent when said statistics are found identical to each other, and the microorganism of interest is determined to be present when said statistics are found to be different.

2. A method of detecting microorganisms according to claim 1, wherein said optical response is the emission of scattered light, the generation of fluorescence, or the combination of the emission of scattered light and the generation of fluorescence from the detected microorganism.

3. A method of detecting microorganisms according to claim 2, wherein the antibody capable of binding specifically to said microorganism is labelled with a fluorescent substance.

4. A method of detecting microorganisms according to claim 1, wherein said microorganism is *Pseudomonas aeruginosa*.

5. A method of detecting microorganisms according to claim 1, wherein said statistic is expressed by a cytogram or a histogram.

6. A method according to claim 1, further comprising:

flowing said suspended substances in said sample; and irradiating said substances with light.

7. A method of detecting microorganisms according to claim 6, wherein said plurality of said microorganisms in said sample are separated and successively flowed by the sheath flow method.

* * * * *